US011918699B2

(12) United States Patent
Chappins

(10) Patent No.: US 11,918,699 B2
(45) Date of Patent: Mar. 5, 2024

(54) METHODS FOR STORING AND CONDITIONING AN EXERCISE MAT

(71) Applicant: Davis S. Chappins, Phoenix, AZ (US)

(72) Inventor: Davis S. Chappins, Phoenix, AZ (US)

(*) Notice: Subject to any disclaimer, the term of this patent is extended or adjusted under 35 U.S.C. 154(b) by 318 days.

(21) Appl. No.: 17/207,051

(22) Filed: Mar. 19, 2021

(65) Prior Publication Data

US 2021/0290807 A1    Sep. 23, 2021

Related U.S. Application Data

(60) Provisional application No. 62/991,688, filed on Mar. 19, 2020.

(51) Int. Cl.
*A61L 2/238* (2006.01)
*A61L 2/232* (2006.01)

(52) U.S. Cl.
CPC ........... *A61L 2/232* (2013.01); *A61L 2202/26* (2013.01)

(58) Field of Classification Search
CPC ....................................................... A61L 2/238
See application file for complete search history.

(56) References Cited

U.S. PATENT DOCUMENTS

| 2012/0227181 A1* | 9/2012 | Cintas | A47G 27/0237 112/475.08 |
| 2016/0129300 A1* | 5/2016 | Moore | B32B 7/05 428/35.5 |
| 2018/0168164 A1* | 6/2018 | Payton | C02F 1/505 |

* cited by examiner

*Primary Examiner* — Donald R Spamer
(74) *Attorney, Agent, or Firm* — Parsons & Goltry, PLLC; Robert A. Parsons; Michael W. Goltry

(57) ABSTRACT

A method includes providing an exercise mat having first and second ends, first and second sides, and first and second major surfaces, providing a pliant substrate including an oligodynamic material having a biocidal or antimicrobial effect, forming a prepared exercise mat by overlying the pliant substrate over the first major surface, the pliant substrate extending across the first major surface between the first side and the second side and between the first end and the second end, and rolling up the prepared exercise mat into a spiral roll including the pliant substrate spiraled between the first major surface and the second major surface, the oligodynamic material contacting, and exerting the biocidal or antimicrobial effect on organisms on or carried by, the first major surface and the second major surface over a period of time while maintaining the prepared exercise mat in the spiral roll.

6 Claims, 10 Drawing Sheets

METHODS FOR STORING AND CONDITIONING AN EXERCISE MAT

CROSS-REFERENCE TO RELATED APPLICATION

This application claims the benefit of U.S. Provisional Patent Application No. 62/991,688, filed Mar. 19, 2020, incorporated herein by reference in its entirety.

FIELD OF THE INVENTION

The present invention relates to exercise mats and, more particularly, to methods for storing and conditioning an exercise mat.

BACKGROUND OF THE INVENTION

Various forms of exercise are commonly performed on exercise mats of rather on the bare floor or ground. Of particular significance are exercise mats of rubber and/or textile specifically designed for yoga, Pilates, and general exercise, which are flat, pliant, portable and easily carried about and can vary in weight, length, thickness, and tackiness.

Yoga exercise mats are designed to be flat, thin, and pliant so they can be rolled up for storage or transport, tacky to prevent hands and feet from slipping, and sufficiently long enough to fit the length of the body while doing a variety of exercises. The standard yoga exercise mat is 68-72 long, although longer ones are available for tall people, and are about 1/16-1/4 of an inch thick. Yoga exercise mats can also be used for Pilates, although there are exercise mats specifically designed for Pilates that are shorter and thicker than yoga exercise mats. General exercise mats are useful for cardio exercises, stretching, crunches, pushups, lunges, and other exercises that require one to be on his belly, back, hands, and knees. The various forms of exercise mats are popular and in common use. Some people own their exercise mats, while others borrow them from the yoga studio, Pilates studio, or gym.

Exercise mats are breeding grounds for bacteria, fungi, viruses, and more because they are often used repeatedly by either the same person or multiple people and exercise rooms are generally a warm environment. Although regularly sanitizing exercise mats before and after use it can help decrease the presence of harmful organisms, they are rarely cleaned, especially before being stored during periods of nonuse, and inevitably become inundated with harmful organisms.

SUMMARY OF THE INVENTION

According to the principle of the invention, a method includes providing an exercise mat having a first major surface and a second major surface, providing a pliant substrate including an oligodynamic material having a biocidal or antimicrobial effect, forming a prepared exercise mat by overlying the pliant substrate over the first major surface, and rolling up the prepared exercise mat into a spiral roll including the pliant substrate spiraled between the first major surface and the second major surface, the oligodynamic material contacting, and exerting the biocidal or antimicrobial effect on organisms on or carried by, the first major surface and the second major surface over a period of time while maintaining the prepared exercise mat in the spiral roll. The method additionally includes unrolling the spiral roll, and separating the substrate from the exercise mat. In another embodiment, the substrate has a pocket, the step of forming the prepared exercise mat additionally includes inserting an end of the exercise mat into the pocket, the step of rolling up the prepared exercise mat into the spiral roll includes rolling up the prepared exercise mat into the spiral roll from the end of the exercise mat inserted into the pocket, and the step of separating the substrate from the exercise mat after unrolling the spiral roll additionally includes withdrawing the end of the exercise mat from the pocket.

According to the invention, a method includes providing an exercise mat having a first end, a second end, a first side, a second side, a first major surface, and a second major surface, providing a pliant substrate including an oligodynamic material having a biocidal or antimicrobial effect, forming a prepared exercise mat by overlying the pliant substrate over the first major surface, the pliant substrate extending across the first major surface between the first side and the second side and between the first end and the second end, and rolling up the prepared exercise mat into a spiral roll including the pliant substrate spiraled between the first major surface and the second major surface, the oligodynamic material contacting, and exerting the biocidal or antimicrobial effect on organisms on or carried by, the first major surface and the second major surface over a period of time while maintaining the prepared exercise mat in the spiral roll. The method additionally includes unrolling the spiral roll, and separating the substrate from the exercise mat. In a particular embodiment, the substrate includes a pocket, the step of forming the prepared exercise mat additionally includes inserting the first end of the exercise mat into the pocket, the step of rolling up the prepared exercise mat into the spiral roll includes rolling up the prepared exercise mat into the spiral roll from the first end of the exercise mat inserted into the pocket, and the step of separating the substrate from the exercise mat after unrolling the spiral roll additionally includes withdrawing the first end of the exercise mat from the pocket.

BRIEF DESCRIPTION OF THE DRAWINGS

Specific objects and advantages of the invention will become readily apparent to those skilled in the art from the following detailed description of illustrative embodiments thereof, taken in conjunction with the drawings in which.

DETAILED DESCRIPTION

Disclosed herein are methods for storing and conditioning an exercise mat.

Figure 1:
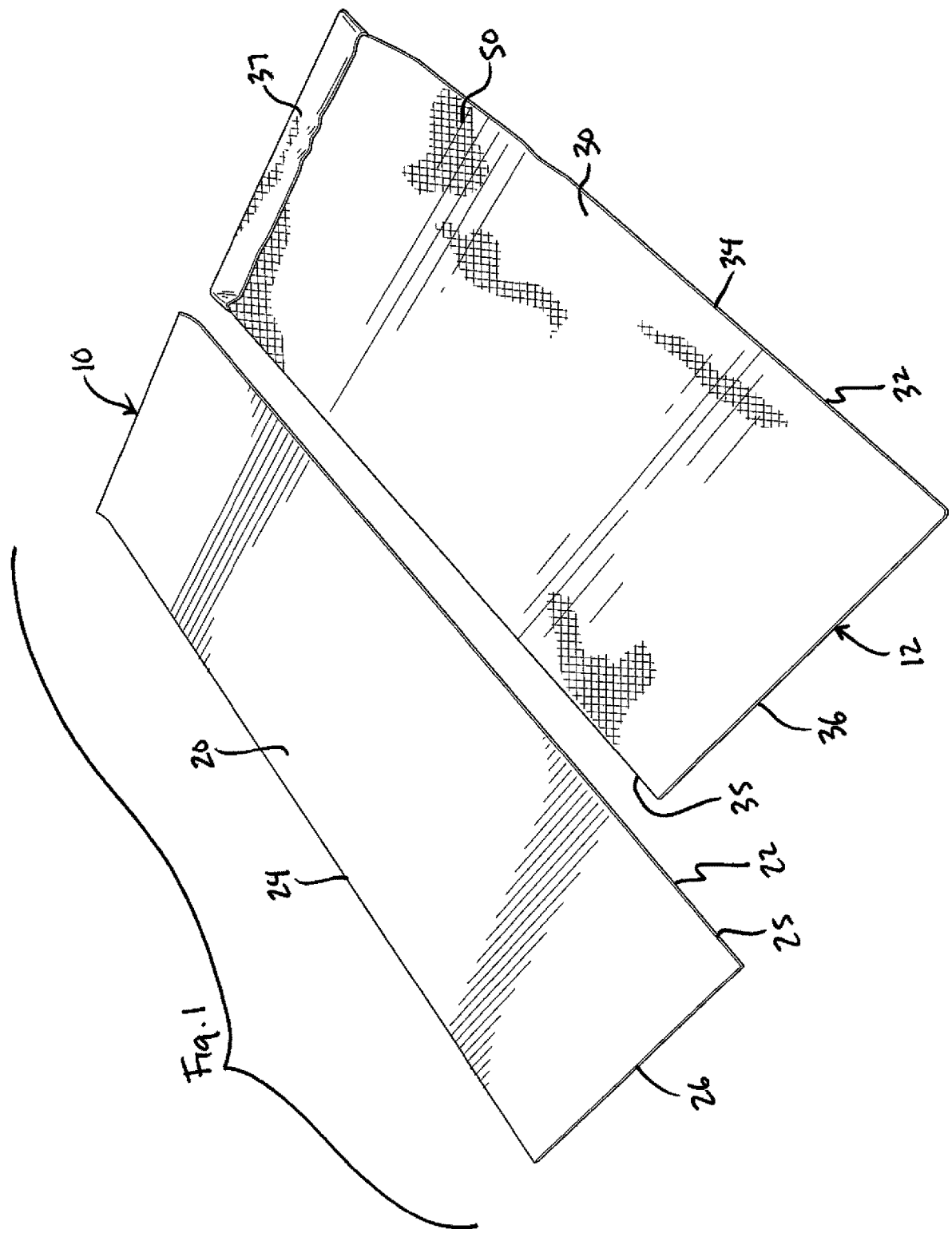
FIG. 1 is a top perspective view of an exercise mat positioned beside a pliant substrate including an oligodynamic material having a biocidal or antimicrobial effect.

Turning now to the drawings, in which like reference characters indicate corresponding elements throughout the several views, attention is directed to FIG. 1 illustrating an exercise mat 10 and a substrate 12. Exercise mat 10 is a standard, readily available, and well-known exercise mat fashioned customarily of natural and/or synthetic rubber and/or one or more natural and/or synthetic textiles according to standard practice and includes opposed major surfaces 20 and 22 and opposed sides 24 and 25 extending between one end 26 of exercise mat 10 and an opposite end 27 of exercise mat 10. Exercise mat 10 is inherently pliant, flat, thin, portable, and customarily rectangular, being long from end 26 to end 27 and comparatively shorter from side 24 to side 25. The flat, thin, and pliant exercise material characteristics of exercise mat 10 enable it to be rolled up from either end 26 or end 27 into a spiral or spiral roll for storage or transport. Exercise mat 10 is tacky according to standard practice to prevent hands and feet from slipping, and sufficiently long from end 26 to end 27 and wide from side 24 to side 25 to accommodate an individual while performing a variety of exercises. Exercise mat 10 has standard dimensions, being approximately 68-72 inches long from end 26 to end 27, 24 inches wide from side 24 to side 25, and about 1/16-1/4 of an inch thick from major surface 20 to major surface 22. The dimensions and exercise material of exercise mat 10 can vary. Exercise mat 10 exemplifies a standard and readily-available exercise mat useful for yoga, Pilates, or general exercise, the details of which are notoriously well-known to the skilled person and not discussed in further detail. Exercise mat 10 is unrolled in FIG. 1 and situated with its major surface 22 down for residing on a floor and major surface 20 upwardly facing for receiving the body of a person thereon engaged in a chosen form of exercise. It is possible to position exercise mat 10 major surface 20 down, leaving its opposed major surface 22 facing upwardly for receiving the body of person thereon engaged in a chosen form of exercise in an alternate embodiment. Exercise mat 10 is useful whether placed major surface 20 down or major surface 22 down.

Figure 2:
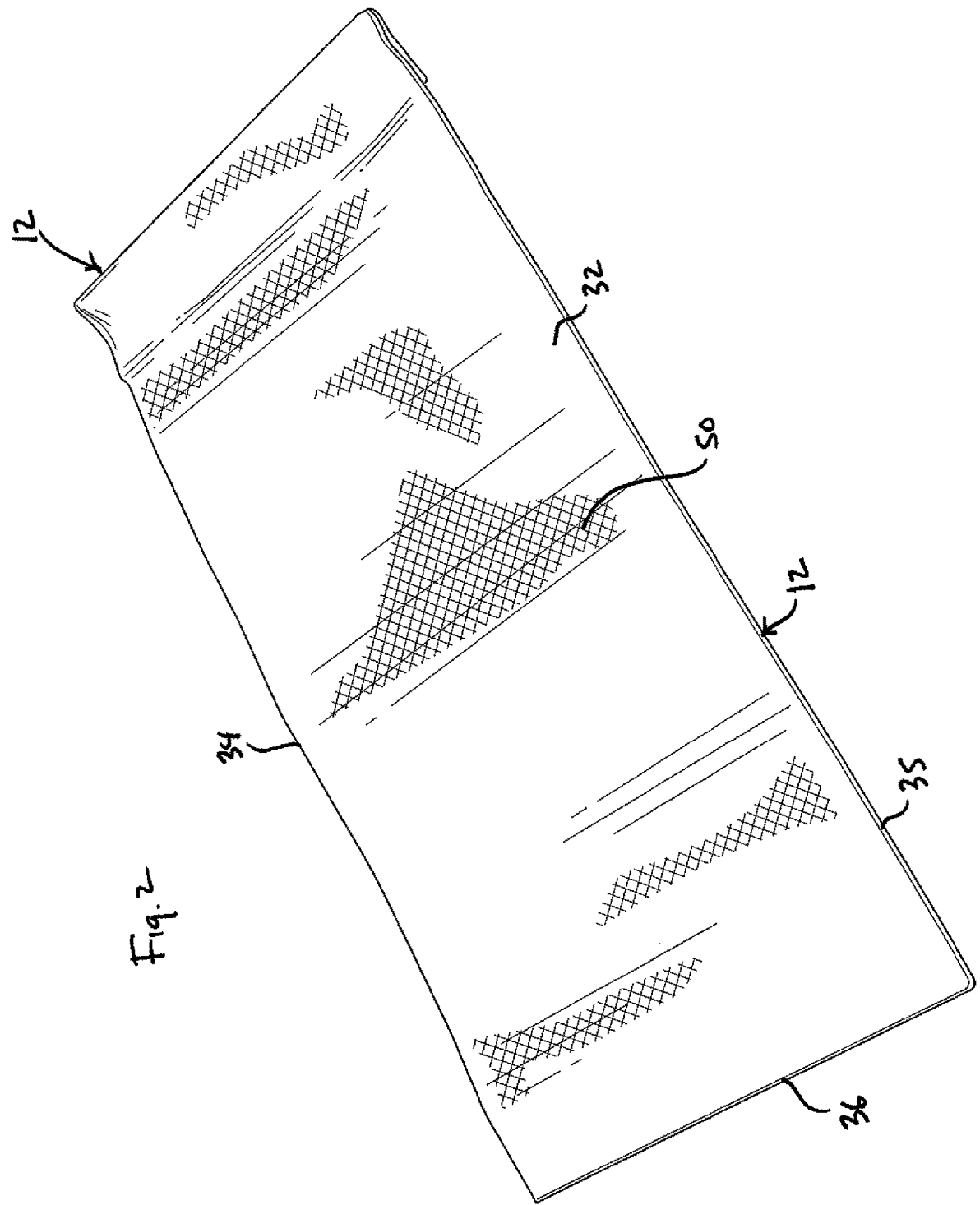
FIG. 2 is a bottom perspective view of the substrate of FIGS. 1.

Referring to FIGS. 1 and 2, substrate 12 includes opposed major surfaces 30 and 32 and opposed sides 34 and 35 extending between one end 36 of substrate 12 and an opposite end 37 of substrate 12. End 37 is a pocket, which is elongate and extends from side 34 to side 35 and open to major surface 30. Substrate 12 is pliant, flat, thin, portable, and rectangular, being long from end 36 to end 37 and comparatively shorter from side 34 to side 35. Substrate 12 is a textile, any inherently pliant, absorbent cloth produced by weaving, knitting, or felting fibers of cotton, wool, polyester, or other chosen natural and/or synthetic fibers or combination of fibers commonly used in the manufacture of known and readily-available textiles/fabrics. The flat, thin, and pliant exercise material characteristics of substrate 12 enable it to be rolled up from either end 36 or end 37 into a spiral or spiral roll for storage or transport. The size of substrate 12 relates to the size of exercise mat 10. In this example, the width of substrate 12 from side 34 to side 25 is slightly wider, 1-5% longer in this embodiment, than the width of exercise mat 10 from side 24 to side 25. The length of substrate 12 from end 36 to end 37 is slightly shorter, 15-20% shorter in this example, than the length of exercise mat 10 from end 26 to end 27. Substrate 12 is about 1/16-1/8 of an inch thick from major surface 30 to major surface 32. Preferably, the width of substrate 12 from side 34 to side 25 is at least as wide as the width of exercise mat 10 from side 24 to side 25, and the length of substrate 12 from end 36 to end 37 is at least as long as a majority of the length of exercise mat 10 from end 26 to end 27. The dimensions of substrate 12 can vary consistent with this disclosure. Substrate 12 is unrolled in FIGS. 1 and 2.

Substrate 12 incorporates an oligodynamic material denoted generally at 50. Oligodynamic material 50 is throughout substrate 12 and has an inherent biocidal or antimicrobial effect on organisms. The oligodynamic material 50 includes one or more metals, especially one or more heavy metals, having the inherent oligodynamic effect. The oligodynamic material 50 is impregnated into substrate 12, coated on substrate 12, or woven or felted into substrate 12. Substrate 12 carries the oligodynamic material 50. In an illustrative embodiment, the oligodynamic material 50 is a standard and well-known silver antimicrobial fabric treatment in/on substrate 12, such as one or more the treatments found under the trademarks PURETEX®, SILPURE®, or ANGIEN®, or SILVADOR® or an equivalent. The oligodynamic material 50 of substrate 12 can also be in other standard forms, such as silver threads, mesh, or nanoparticles in alternate embodiments. Silver is a preferred metal of the oligodynamic material 50. Substrate 12 can incorporate copper, zinc, and/or one or more other suitable oligodynamic metals with or without the presence of silver without departing from the invention.

A method of conditioning exercise mat 10 inherently being in need of conditioning such after repeated or prolonged use is disclosed. The method includes forming a prepared exercise mat 60 in FIG. by overlying substrate 12 over major face 20 of exercise mat 10, and rolling up the prepared exercise mat 60 into a spiral roll 65 in FIGS. 9 and 10 including substrate 12 spiraled between major surfaces 20 and 22, the oligodynamic material 50 contacting, and exerting the biocidal or antimicrobial effect on organisms on or carried by, major surfaces 20 and 22 at the same time over a period of time while maintaining the prepared exercise mat 60 in the configuration of spiral roll 60. After the chosen period of time has elapsed, the spiral roll 65 is unrolled and the substrate 12 is separated from exercise mat 10. This process is repeated after each use of exercise mat or as otherwise desired.

Figure 3:
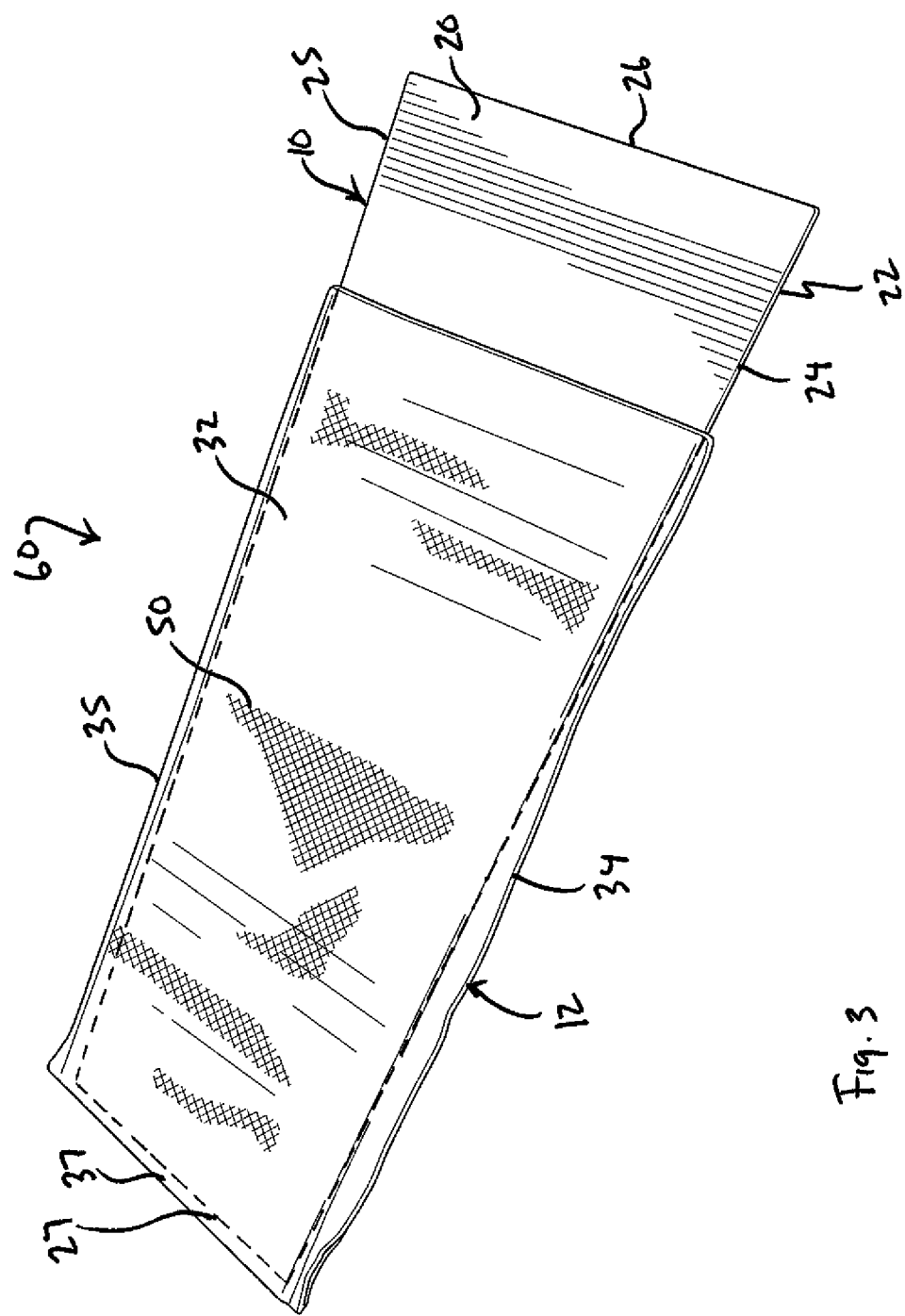
FIG. 3-10 illustrate a sequence of steps of conditioning the exercise mat with the pliant substrate of FIG. 1.
Figure 4:
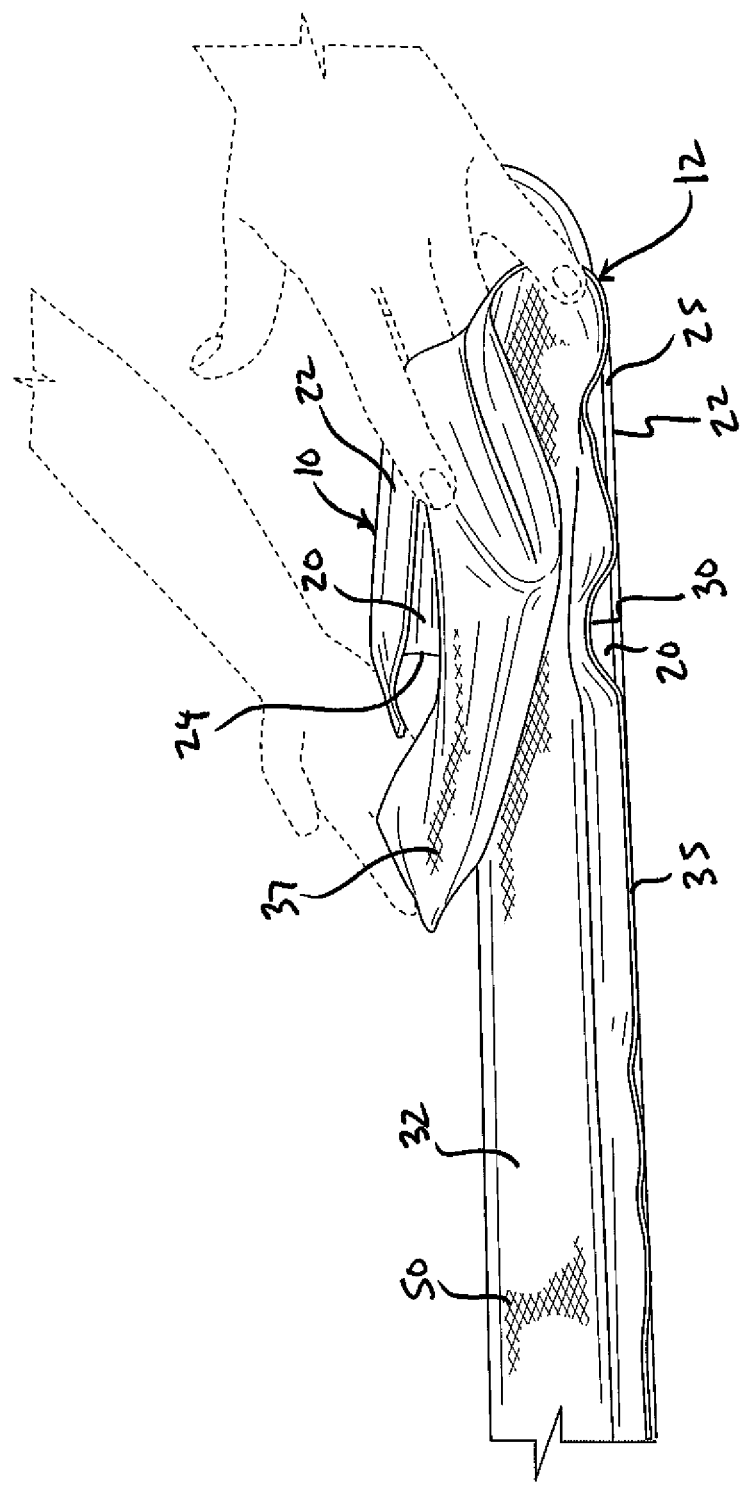

In a preferred embodiment, the prepared exercise mat 60 in FIG. 3 is formed by overlying substrate 12 flatwise over major surface 20 of exercise mat 10, substrate 12 extending across major surface 30 of exercise mat 10 between its sides 24 and 25 and ends 26 and 27. In this embodiment, substrate 12 is placed major surface 30 down over major surface 20 of the unrolled exercise mat 20. Both substrate 12 and exercise mat 10 are flattened or otherwise spread out in FIG. 3, and major surface 30 of substrate 12 covers and contacts major surface 20 of exercise mat 10 between sides 24 and 25 and between ends 26 and 27 of exercise mat 10. Ends 27 and 37 are juxtaposed, sides 24 and 34 are juxtaposed, and sides 25 and 35 are juxtaposed. Major surface 30 of substrate 12 extends across the width of major surface 20 of exercise mat 10 from side 24 to side 25 and the length of major surface 20 from end 27 of exercise mat 10 to end 36 of substrate 12 proximate to end 26 of exercise mat 10. Substrate 12 can be sized to completely extend across the width and length of major surface 20 of exercise mat 10 in an alternate embodiment. In the preparation of prepared exercise mat 60, end 27 of exercise mat 10 is preferably inserted into pocket 37 by hand FIG. 4 before flattening or spreading out the prepared exercise mat 10 in FIG. 5. The insertion of end 27 of exercise mat 10 into pocket 37 serves to initially couple substrate 12 to exercise mat 10 to provide a measure of attachment and stability. The prepared exercise mat 60 is then rolled up by hand widthwise into spiral roll 65 in FIGS. 9 and 10.

Figure 5:
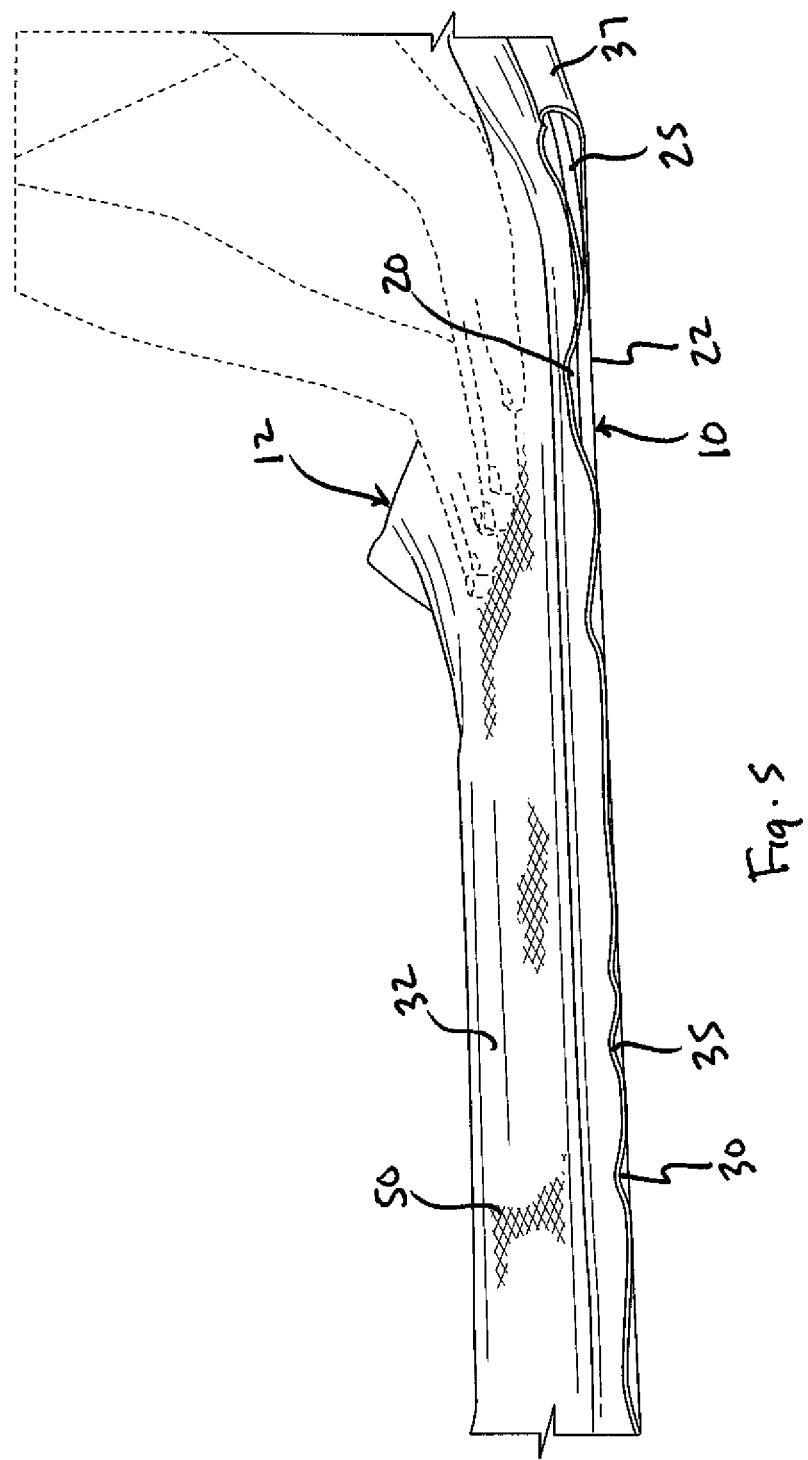
Figure 6:
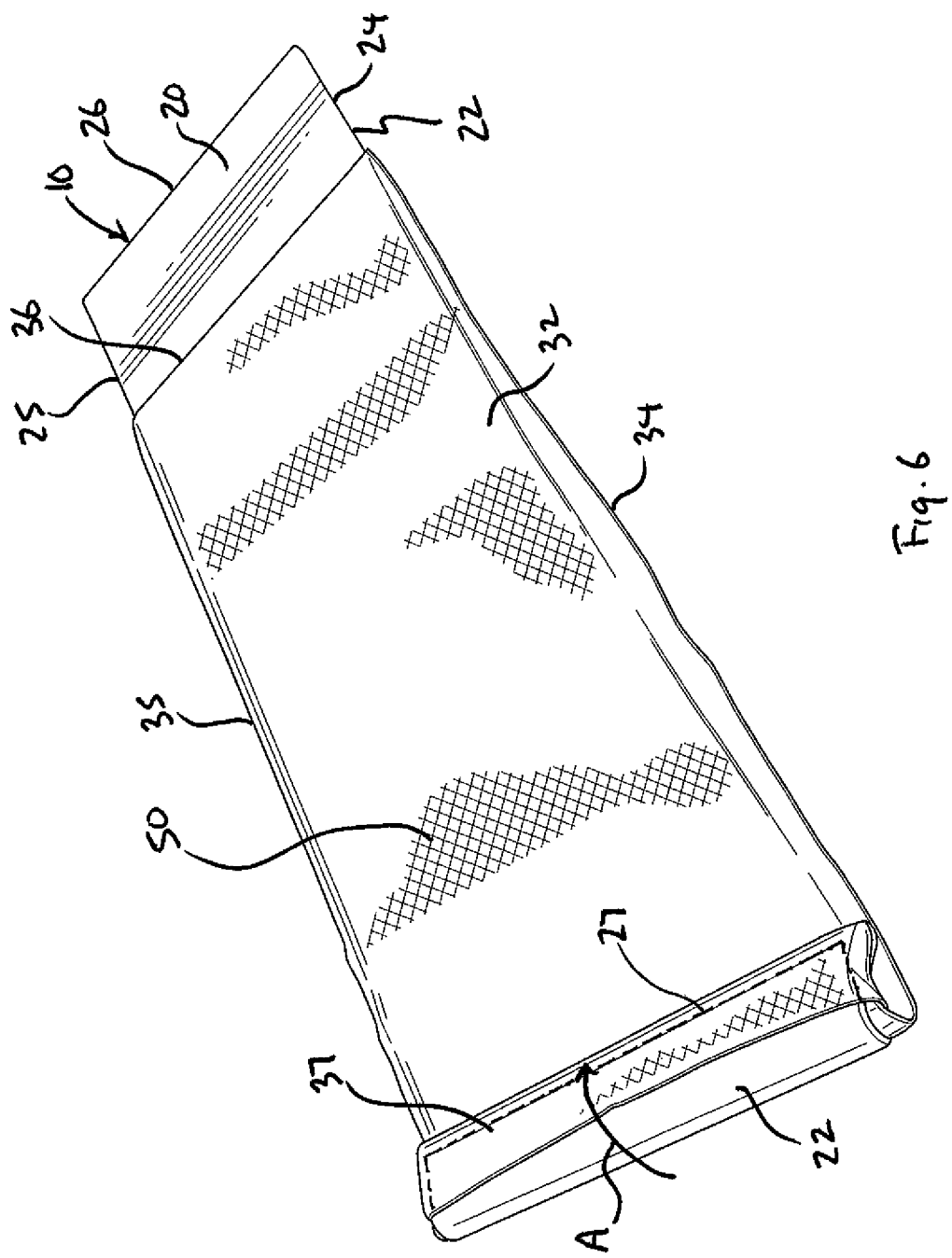
Figure 7:
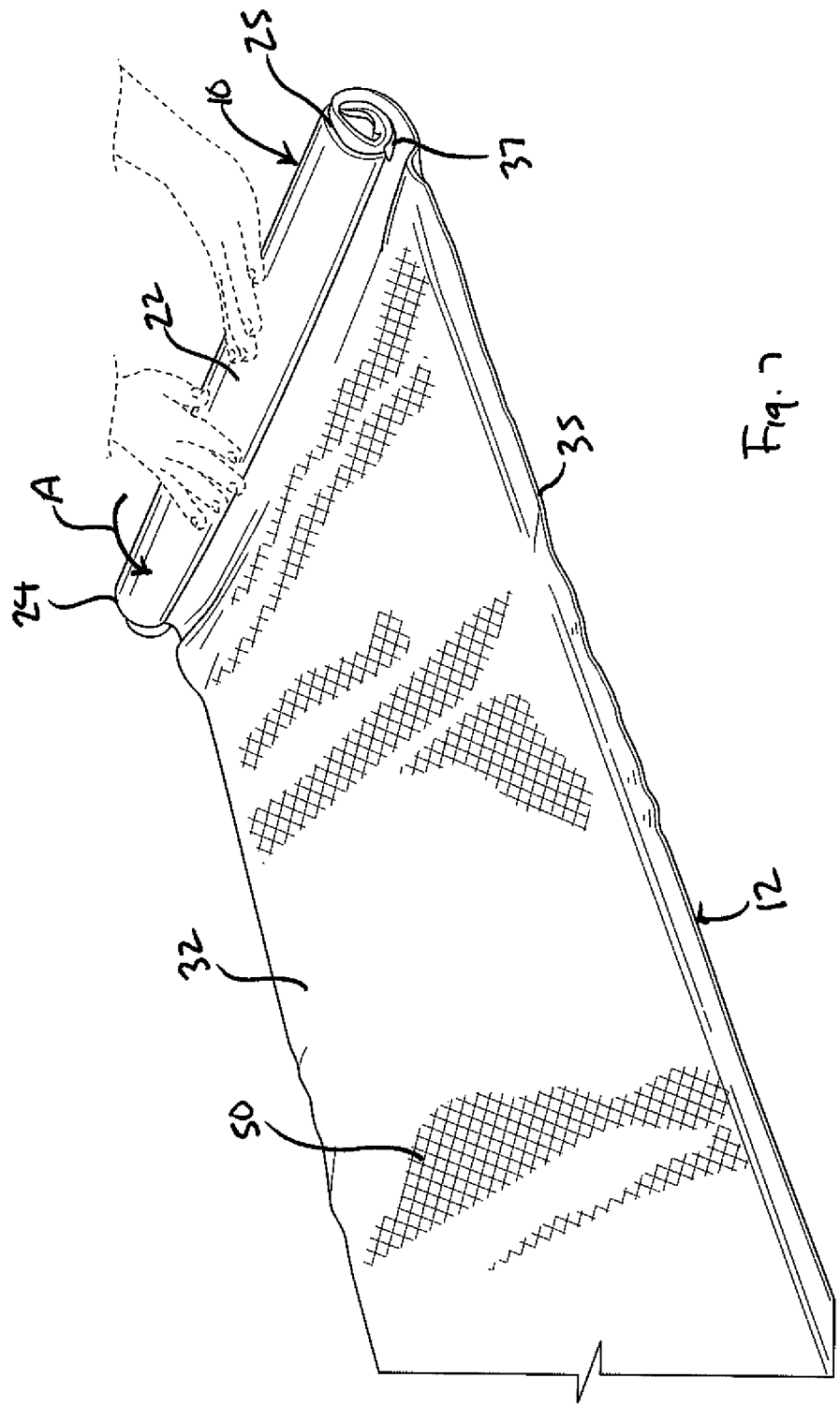
Figure 8:
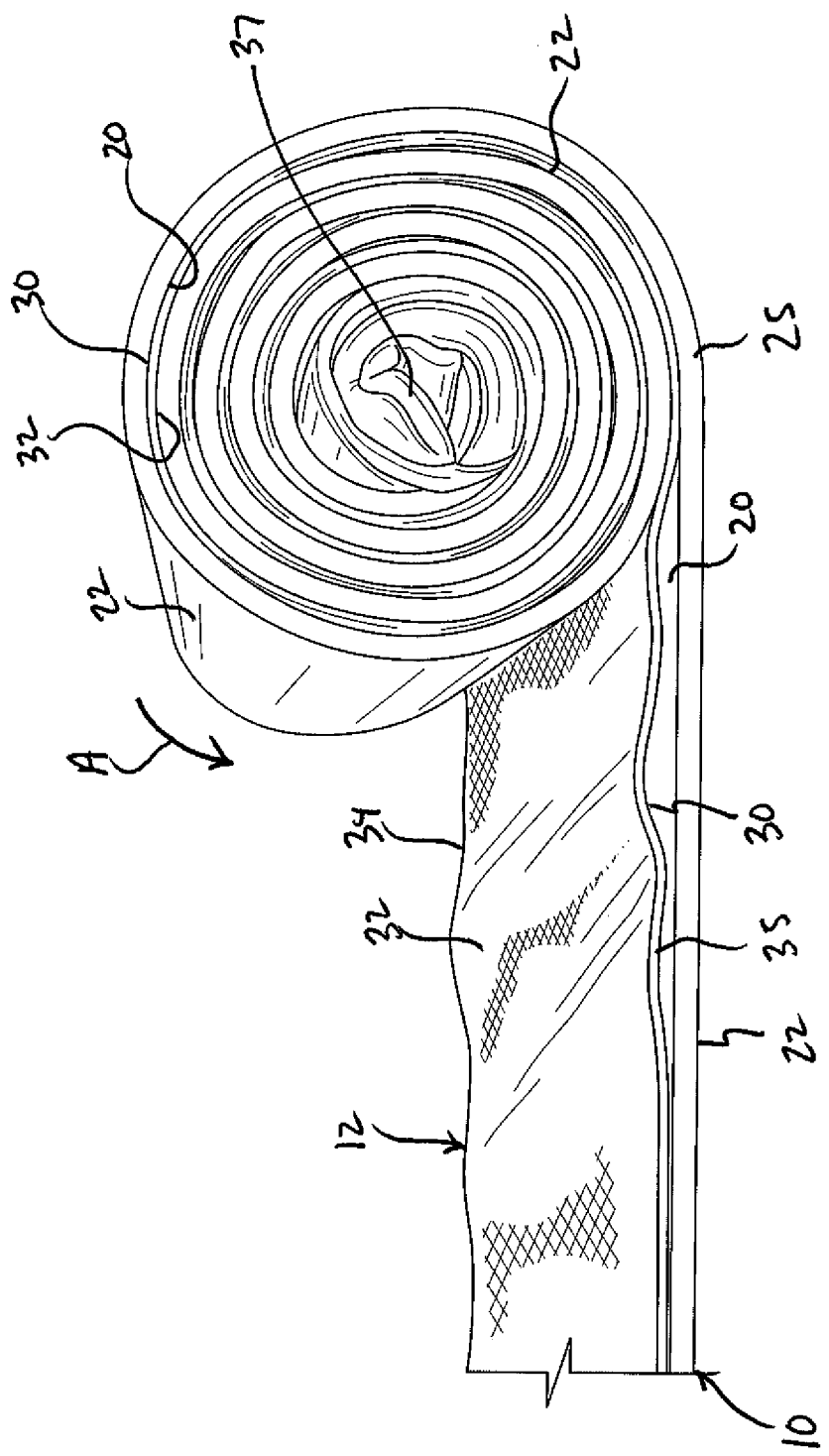
Figure 9:
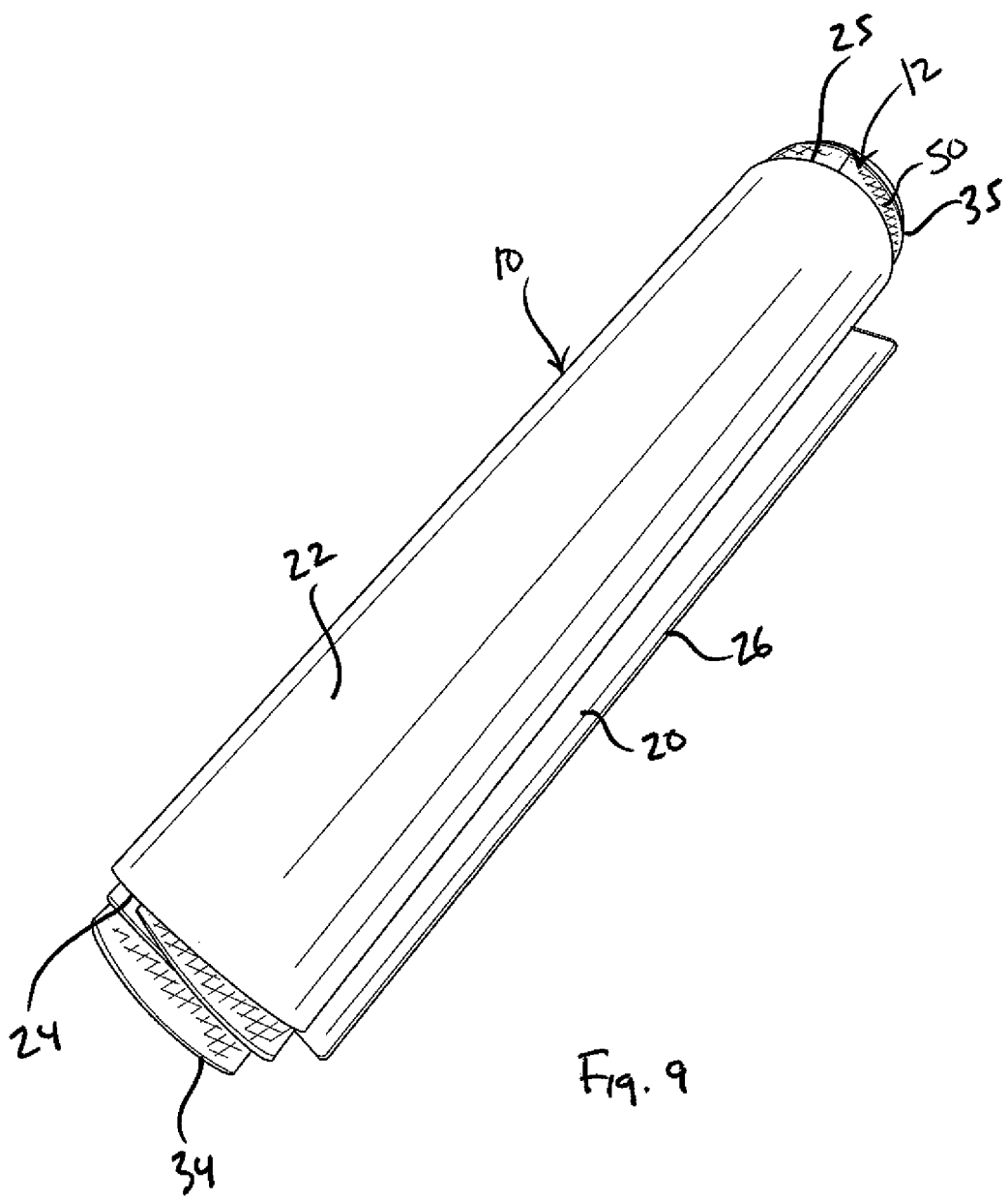
Figure 10:
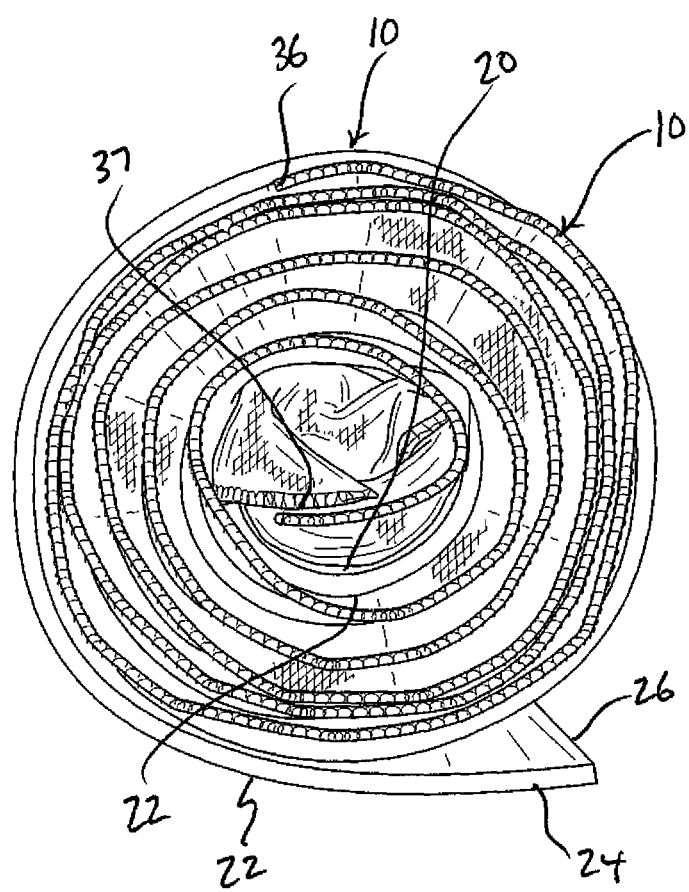

Starting from end 27 of exercise mat 10 inserted into pocket 37 in FIG. 5 in accordance with a preferred embodiment, the prepared exercise mat 60 is rolled up widthwise in the direction of arrow A in FIGS. 6, 7, and 8 major surface 22 down tightly over major surface 32 of substrate 12 into spiral roll 65 in FIGS. 9 and 10. In spiral roll 65, exercise mat 10 and substrate 12 are spiraled together widthwise along their respective lengths, substrate 12 is spiraled between spiraled major surfaces 20 and 22 of exercise mat 10, and the oligodynamic material 50 of substrate directly contacts, and exerts the biocidal or antimicrobial effect on organisms on or carried by, major surfaces 20 and 22 of exercise mat over a period of time while maintaining the prepared exercise mat 60 in FIG. 3 in the form of spiral roll 65 in FIGS. 9 and 10. When prepared exercise mat 60 is rolled up into spiral roll 65, it is rolled up sufficiently tight major surface 22 down over major surface 32 of substrate 12 to keep spiraled major surface 30 and the oligodynamic material 50 of substrate 12 in direct contact against the spiraled major surface 20 of exercise mat 10 between the sides 24 and 25 and ends 26 and 27 of exercise mat 10, and to bring spiraled major surface 32 and the oligodynamic material 50 of substrate 12 into direct contact against the spiraled major surface 22 of exercise mat 10 between sides 24 and 25 and ends 26 and 27 of exercise mat 10. This direct contact of spiraled major surface 30 and the oligodynamic material 50 of substrate 12 against spiraled major surface 20 of exercise mat 10 and spiraled major surface 32 and the oligodynamic material 50 of substrate 12 against spiraled major surface 22 of exercise mat 10 in spiral roll 65 enables the oligodynamic material 50 to concurrently exert its inherent biocidal or antimicrobial effect on organisms on or carried by major surfaces 20 and 22 of exercise mat 10 over a period of time while exercise mat 10 and substrate 12 are stored in the form of spiral roll 65. In an illustrative example, the spiral roll 65 is conveniently stored to permit the oligodynamic material 50 to exert the inherent biocidal or antimicrobial effect on organisms on or carried by exercise mat 10 over a period of time sufficient to at least partially disinfect exercise mat 10, such as overnight, i.e., for the duration of night, or other period of time when exercise mat 10 is not in use. The configuration of spiral roll 65 is important because it enables substrate 12 spiraled together with exercise mat 10 to exert is inherent biocidal or antimicrobial effect on both major surfaces 22 and 22 at the same time. Although exercise mat 10 can be periodically cleaned, storing it maintained in spiral roll 65 during periods of nonuse is an easy and efficient way to condition exercise mat 10 by at least partially disinfecting it without the need to wipe it down or wash it with soap and water. In an alternate embodiment, prepared exercise mat 60 can be rolled up major surface 32 of substrate 12 down tightly over major surface 22 of exercise mat 10 into a spiral roll 65. In either embodiment, exercise mat 10 is released from substrate 12 by reversing the above operation, by unrolling the superimposed layers 60, withdrawing end 27 of exercise mat 10 from pocket 37, and separating substrate 12 from exercise mat 10. While the prepared exercise mat 10 is rolled up widthwise into spiral roll 65 in FIGS. 9 and 10 along the respective lengths of exercise mat 10 and substrate 12, it can be rolled up by lengthwise into a spiral roll 65 along the respective widths of exercise mat 10 and substrate 12.

Prepared exercise mat 60 can be rolled up major surface 32 of substrate 12 down tightly over major surface 22 of exercise mat 10 into a spiral roll 65 in an alternate embodiment. Further, a prepared exercise mat can be formed by placed major surface 30 down over major surface 20 of the unrolled exercise mat 20 so substrate 12 covers major surface 20 of exercise mat 10 between sides 24 and 25 and ends 26 and 27, ends 26 and 37 are juxtaposed, sides 24 and 34 are juxtaposed, sides 25 and 35 are juxtaposed, and major surface 30 of substrate 12 extends across major surface 20 of exercise mat 10 from end 37 to end 36 proximate to end 27 of exercise mat 10. In this embodiment, the formed prepared exercise mat can be rolled up widthwise into a spiral roll along the respective lengths of exercise mat 10 and substrate 12, or lengthwise into a spiral roll along the respective widths of exercise mat 10 and substrate 12.

Although exercise mat 10 and substrate 12 are assembled into the prepared exercise mat 60 by overlying substrate 12 major surface 30 down over major surface 20 of exercise mat 10, a prepared exercise mat can be formed by overlying substrate 12 major surface 30 down over major surface 22 of exercise mat 10. If desired, substrate 12 can be formed with one or more straps or fasteners configured releasably secure the rolled configuration of exercise mat 10 and substrate 12.

The present invention is described above with reference to illustrative embodiments. However, those skilled in the art will recognize that changes and modifications may be made in the described embodiments without departing from the nature and scope of the present invention. For instance, in an alternate embodiment, the oligodynamic material of substrate 12 is electrically connected to a suitable power source, such as an AC or DC power source. When the power source is engaged, it charges the oligodynamic material, which increases the oligodynamic effect. In an illustrative embodiment, the oligodynamic material of substrate 12 is in the form of threads or mesh electrically connected to the chosen power source using techniques well-known to the skilled electrician.

Various further changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A method of conditioning an exercise mat in need of conditioning after repeated or prolonged use thereof, the exercise mat having a first major surface and a second major surface, the method comprising:
   providing a pliant substrate comprising an oligodynamic material having a biocidal or antimicrobial effect;
   forming a prepared exercise mat by overlying the pliant substrate over the first major surface;
   rolling up the prepared exercise mat into a spiral roll comprising the pliant substrate spiraled between the first major surface and the second major surface, the oligodynamic material contacting, and exerting the biocidal or antimicrobial effect on organisms on or carried by, the first major surface and the second major surface during a duration of nonuse of the exercise mat while maintaining the prepared exercise mat in the spiral roll, at least partially disinfecting the exercise mat without the need to wipe down or wash the exercise mat; and
   unrolling the spiral roll and separating the substrate from the exercise mat after the duration of nonuse.

2. The method according to claim 1, wherein:
   the substrate having a pocket;
   the step of forming the prepared exercise mat additionally includes inserting an end of the exercise mat into the pocket; and
   the step of rolling up the prepared exercise mat into the spiral roll comprises rolling up the prepared exercise mat into the spiral roll from the end of the exercise mat inserted into the pocket.

3. The method according to claim 2, further comprising:
   wherein the step of unrolling the spiral roll and separating the substrate from the exercise mat includes withdrawing the end of the exercise mat from the pocket and separating the substrate from the exercise mat.

4. A method of conditioning an exercise mat in need of conditioning after repeated or prolonged use thereof, the exercise mat having a first end, a second end, a first side, a second side, a first major surface, and a second major surface, the method comprising:

provyding a pliant substrate comprising an oligodynamic material having a biocidal or antimicrobial effect;

forming a prepared exercise mat by overlying the pliant substrate over the first major surface, the pliant substrate extending across the first major surface between the first side and the second side and between the first end and the second end;

rolling up the prepared exercise mat into a spiral roll comprising the pliant substrate spiraled between the first major surface and the second major surface, the oligodynamic material contacting, and exerting the biocidal or antimicrobial effect on organisms on or carried by, the first major surface and the second major surface during a duration of nonuse of the exercise mat while maintaining the prepared exercise mat in the spiral roll, at least partially disinfecting the exercise mat without the need to wipe down or wash the exercise mat; and unrolling the spiral roll and separating the substrate from the exercise mat after the duration of nonuse.

5. The method according to claim 4, wherein:

the substrate having a pocket;

the step of forming the prepared exercise mat additionally includes inserting the first end of the exercise mat into the pocket; and the step of rolling up the prepared exercise mat into the spiral roll comprises rolling up the prepared exercise mat into the spiral roll from the first end of the exercise mat inserted into the pocket.

6. The method according to claim 5, further comprising:

wherein the step of unrolling the spiral roll and separating the substrate from the exercise mat includes withdrawing the first end of the exercise mat from the pocket and separating the substrate from the exercise mat.

\* \* \* \* \*